United States Patent [19]
von Redwitz

[11] Patent Number: 5,024,526
[45] Date of Patent: Jun. 18, 1991

[54] MEASURING INSTRUMENT FOR DETERMINING THE SCATTERING AND ABSORPTION COEFFICIENT OF THE ATMOSPHERE

[75] Inventor: Heribert von Redwitz, Starnberg, Fed. Rep. of Germany

[73] Assignee: Deutsche Forschungs- und Versuchsanstalt fur Luft- und Raumfahrt e.V., Cologne, Fed. Rep. of Germany

[21] Appl. No.: 333,392

[22] Filed: Apr. 5, 1989

[30] Foreign Application Priority Data

Apr. 6, 1988 [DE] Fed. Rep. of Germany ....... 3811475

[51] Int. Cl.$^5$ ..................... G01N 21/47; G01N 21/59; G01N 1/02
[52] U.S. Cl. ..................................... 356/73; 356/339; 356/432
[58] Field of Search ...................... 356/73, 432, 432 T, 356/437, 438, 439, 338, 339; 250/343, 564, 574

[56] References Cited

U.S. PATENT DOCUMENTS

| | | | |
|---|---|---|---|
| 3,994,603 | 11/1976 | Paschedag | 356/442 |
| 4,231,661 | 11/1980 | Walsh et al. | 356/340 |
| 4,245,910 | 1/1981 | Källander | 356/338 |
| 4,277,179 | 7/1981 | Bruce | 356/439 |
| 4,818,882 | 4/1989 | Nexo et al. | 356/432 |

FOREIGN PATENT DOCUMENTS

| | | | |
|---|---|---|---|
| 2254764 | 6/1974 | Fed. Rep. of Germany | |
| 2711555 | 9/1978 | Fed. Rep. of Germany | |
| 3008183 | 9/1980 | Fed. Rep. of Germany | |
| 50141 | 4/1980 | Japan | 356/439 |
| 42842 | 3/1982 | Japan | 356/438 |
| 871125 | 10/1981 | U.S.S.R. | 356/437 |

OTHER PUBLICATIONS

"Staub-Reinhalt. Luft", [Clearing of the Air by Dust] 32, 1972, No. 12, p. 513, Streulicht-Teilchenzähler mit Spezialoptic, [Scattered Light Particle Counter with Special Optics], by Hans Hilgers.
"Applied Optics", vol. 21, No. 1, 1982, pp. 90–93, Photoacoustic Cell Using Elliptical Acoustic Focusing, by Jean-Marc Heritier, J. E. Fouquet and A. E. Siegman.
Von G. H. Ruppersberg, "Registrierung der Sichtweite mit dem Streulichtschreiber", [Recording of Visual Range with the Scattered Light Plotter], reprint from, Beiträge zur Physik der Atmosphäre, [Atmospheric Physics Journal] 37, 3/4, 1964, pp. 252–263.
R. G. Beuttell and A. W. Brewer, "Instruments for the Measurement of the Visual Range", Journal of Scientific Instruments 26 (1949), pp. 357–359.
R. J. Charlson, H. Hovath and R. F. Pueschel, "The Direct Measurement of Atospheric Light Scattering Coefficient for Studies of Visibility and Pollution", Atmospheric Environment, (1967), vol. 1, pp. 469–478.

Primary Examiner—Richard A. Rosenberger
Attorney, Agent, or Firm—Browdy and Neimark

[57] ABSTRACT

A measuring instrument for simultaneous in situ determination of the spectral scattering and absorption coefficient, which can also be called an extinction meter, has a modulated light source and an optical system encompassing the hemisphere; the optical system has a multiply folded ray path with a focal point in the volume to be measured, and through this system the measurement signal is projected to detectors. The scattering measurement signals, which are maximally enlarged in this way, are then separated from those for the absorption. The extinction meter also has not only an integrating nephelometer for monitoring purposes but also a transmission meter for low transmission factors. Because of the small three-dimensional size and the streamlined shape of the measuring portion of the extinction meter, the extinction meter can be carried in aircraft and surface vehicles. Because of the disposition of the optical system, the error in the measurement values is negligible, in comparison with other instruments with which only the scattering coefficient can be determined. Moreover, the calibration value during a measurement phase can be determined both automatically and manually. Contamination of the instrument with gas to be measured is reduced, by the stabilization of a turbulence ring by means of baffles. Moreover, interference with the flowing aerosol on the part of the instrument is largely eliminated via a hoop-like hood functioning like a wing-tip slot.

20 Claims, 3 Drawing Sheets

MEASURING INSTRUMENT FOR DETERMINING THE SCATTERING AND ABSORPTION COEFFICIENT OF THE ATMOSPHERE

BACKGROUND OF THE INVENTION

1. Field of the Invention

The invention relates to a measuring instrument for determining the scattering and absorption coefficient of the atmosphere, having a light emitter on the emitter side, and on the receiver side having a light detector and an infrared sound receiver for emitter light attenuated in the atmosphere, and having instruments for measuring the intensity of the received, scattered light and the absorbed light. In this document, such a measuring instrument will also be called an extinction meter.

2. The Prior Art

An extinction coefficient is made up of the sum of a spectral scattering coefficient and an absorption coefficient; these coefficients are important basic variables of the atmosphere. Flight tests of these basic variables determined by means of an extinction meter, or in other words measurements of such variables made from aircraft, are of particular significance for assessing the anthropogenic and natural loading of the air for lidar measurements, for a radiation balance, for optical depth, icing, turbulence, visibility, slant range visibility, and so forth.

Conventional instruments function either as visual range or scattered light meters and typically include an integrating nephelometer. Transmissometers must measure through a distance that is adapted to the measured value. Scattered light meters, also known as integrating nephelometers, in which the scattering in the atmosphere is summed up over a wide range of angles, have been known for a long time. This kind of scattered light plotter is for instance described by G. H. Ruppersberg in an article entitled "Registrierung der Sichtweite mit dem Streulichtschreiber" [Recording of Visual Range with the Scattered Light Plotter], issued as a reprint from "Beiträge zur Physik der Atmosphäre" [Atmospheric Physics Journal] 37, ¾, 1964, pp. 252-263, published by the Akademische Verlagsgesellschaft Frankfurt am Main, 1964. An integrating nepheloemeter is discussed both by R. G. Beuttel and A. W. Brewer in "Instruments for the Measurement of the Visual Range" in the Journal of Scientific Instruments 26 (1949), pp. 357-359 and by R. J. Charlson, H. Horvath and R. S. Pueschel in "The Direct Measurement of Atmospheric Light Scattering Coefficient for Studies of Visibility and Pollution", Environment, Vol. 1, pp. 469-478.

With these instruments, however, only the scattering coefficient, but not the extinction coefficient, can be measured; the extinction coefficient must be measured exactly, for instance for a visibility determination by the Koschmieder theory, because the absorption cannot be determined with these instruments.

For specialized probes of the atmosphere, aircraft-worthy integrating nephelometers are needed (that is, integrating nephelometers that can be accommodated in or on aircraft) which vary the aerosol to be measured as little as possible. Such variations may for instance arise from heating and/or turbulence; moreover, a flow in curved channels can cause a false reading of the particle size distribution, as is the case with equipment on the market or modified research equipment.

Known aircraft-worthy integrating nephelometers also lack genuine calibration during the measurement. Although measurement takes place over a wide range of angles, it is not done below and above an angle of 9° and 170° respectively. The maximum for the integrant of the condition equation for the absolute scattering function with the aid of which the scattering coefficient can be ascertained occurs at approximately 10° to 20° for average scattering functions.

SUMMARY OF THE INVENTION

It is accordingly an object of the present invention to devise a measuring instrument for measurement or simultaneous in situ determination of the spectral scattering and absorption coefficient at variable wavelengths, or in other words at wavelengths that can be varied successively, in alternation, or automatically. Furthermore, the measuring instruments devised by the invention should enable the most undisturbed flow possible of the aerosol to be measured through it and should also be suitable for relatively small instrument carriers, such as aircraft.

According to the invention, in an instrument as generically defined above, this is attained by providing as the light source of the light emitter, a pulsed modulated laser or a pulsed and modulated laser diode having a device for varying the frequency or doubling the frequency or having a device which has discontinuously frequency intervals of the discrete frequencies. An annular mirror is provided having an inlet slit and a diametrically opposed outlet slit for the introduction and the exiting of the aerosol or attenuating gas be measured, and a portion of a rotationally symmetrical ellipsoidal mirror is disposed such that the first focal point of the ellipsoidal mirror is located in the center point of the center line of the annular mirror and its second focal point is located in the middle of the light detector and the sound receiver associated with it, both of which detectors are accommodated in a streamlined space, so that radiation of a sufficiently small divergence emitted by the light emitter is reflected multiply, after its introduction to the annular mirror. The ray segments of this mirror break concentrically about the first focal point of the ellipsoidal mirror, via which point the aerosol or attenuating gas to be measured, flowing from the inlet to the outlet slit in the annular mirror, is carried. Advantageous further features of the invention are the subject of the dependent claims.

In the invention, the wavelengths can be varied; a temporal resolution or repetition rate, a resultant spatial resolution or repetition rate when the extinction meter is moved, as well as the instant or order of the calibration process and dark calibration, are also performed either automatically or manually during the measurement. In the invention, the individual measured values and setting parameters are then associated with channels, stored in memory and sampled, and either read off directly from a display or recorded on a magnetic tape. By further processing of the spectral scattering and absorption coefficient with the aid of a computer, variables derived at suitable wavelengths are obtained, with which assessments can be made as to both the type and the mass concentration of the aerosol measured. These time- or location-dependent profiles are preferably displayed in the form of color-coded images, which facilitates evaluation of the measured air masses in an objective comparison.

As an example, a measurement flight at a constant altitude through an air mass will be shown and described. The measured values and the variables derived from them, such as the scattering and absorption coefficient at various wavelengths, the associated concentration, the type of measured aerosol, and so forth, are then plotted in horizontal bands of various colors as a function of time or location. The amount of the measured value or of the derived variables is encoded by means of the color saturation. In a simplified version, the entire picture can also be reproduced in grey values, in which case the measured values can be found at the location of the ordinate, using a predetermined key.

With the measuring instrument according to the invention, measurements can be performed at angles of approximately 4° to approximately 176°. The measurement accuracy is increased by providing that the measurement signal is increased when the proportions in the case of pronounced forward scattering (that is, small angles in the case of Mie scattering) and in the case of a forward and backward scattering (that is, large angles in the case of Rayleigh scattering) are taken into consideration and the calibration is performed automatically, and sufficiently frequently. The calibration is effected with the aid of a calibrated scattering body during the measurement, and the calibration value is intended here to be from one to two powers of ten above the maximum expected measurement signal.

Given a sufficiently temperature-stabilized light source and suitable detectors, it is then sufficient to measure both the simulated dark/light pulse which is additive to the measurement signal and a sound or infrared pulse automatically in the dark phase during the measurement, if linearity can be assumed to prevail. In the extinction meter according to the invention, a trigger signal of a pulsed laser or a pulsed diode then controls an electronic switch, such that it is open, but only during the time intervals during which the signal of the corresponding detector arrives; via an electronic time delay element, the transit time of the sound pulse is also taken into account.

For the so-called null pulse by means of which the background or dark current is measured, an identical trigger signal is also simulated via a timing unit. In the remaining time, a ground connection is established via a switch, so that only the pulses of the light and sound detectors, but not interfering pulses, are processed further. For instance, the constant light portion is electrically separated from the measured signal by means of capacitive subtraction. The final signal is selected from the noise component by suitable filtering, and after that, the component of the dark pulse is also electronically subtracted from the signal.

In the measurement of the spectral scattering and absorption coefficient, it should be noted that in an interaction with material, absorption is the conversion of radiant energy into a different form of energy, while scattering, in an interaction with material or in a passage through a medium, is the deflection of directional radiation in various directions. The sum of the radiation that extends in all directions from a scatter volume is equal to the attenuation of the radiation extending straight ahead in which no absorption takes place. The absolute volumetric scattering function indicates the angular distribution of the scattered radiation with respect to the primary direction; if this scattering function is weighted with an angle function and integrated over the range of a hemisphere, this method leads to the scattering coefficient that is sought, which takes asymmetrical spatial scattering functions into account.

In a known apparatus, the scatter volume to be tested is irradiated by means of a bunch of radiation which originates at an externally located light point source and extends over a wide angular range in a sine wave, but this angular range encompassing only the semicircle. The radiation intensity of the scattered radiation out of this angular range is detected and measured in one direction by means of receiver optics having a small opening angle opposite a black light trap. The scattered radiation in other directions is subtracted here. A reversal of the optical beam path is obtained by the other apparatus. The scatter volume to be measured is irradiated with a bundle of rays, and the scatter volume is detected and measured by externally located receiver optics having a large opening angle lengthwise of the radiation bundle in a wide angular range which, however, encloses only the semicircle. Because of the length, however, the "angle of view" of the optics in the direction of a black light trap is achievable only with difficulty. Neither apparatus is capable of taking asymmetrical scattering functions into account. Because of given geometric conditions, an angular range encompassing the semicircle is not attainable in either version. In accordance with a limited opening angle of the receiver optics, only a fraction of the radiant intensity of the scattered radiation of the aerosols or molecules in the scatter volume, which scatter in all directions, is detected and measured. The solid angle of a lens or lens system having a relative opening of 1:2.8 amounts to only 1.6% of the solid angle that the hemisphere represents.

Each scattering particle here furnishes a scattering component only within the opening angle or below the angle from which it appears, and does so continuously only for a scattering angle corresponding to the scattering angle range at the time. The angle of the scattered radiation is dependent, in both embodiments of the invention, on the particular location of the scatter volume.

In the exemplary embodiment of the measuring instrument according to the invention, the scattered radiation, or the sound pulse generated in the absorption as well as the infrared radiation of the scatter volume is detected over virtually the entire hemisphere to an extent of approximately 95%, in other words including asymmetrical scattering functions; the angle of the scattering and infrared or sound radiation, however, is not dependent on the location of the scatter volume. Because of this factor, and because of the n-multiple irradiation of the test volume, the scatter volume can be designed to be small in terms of its dimensions.

BRIEF DESCRIPTION OF THE DRAWINGS

The invention will now be described in terms of preferred exemplary embodiments, referring to the enclosed drawings, in which.

DESCRIPTION OF THE PREFERRED EMBODIMENTS

Figure 1:
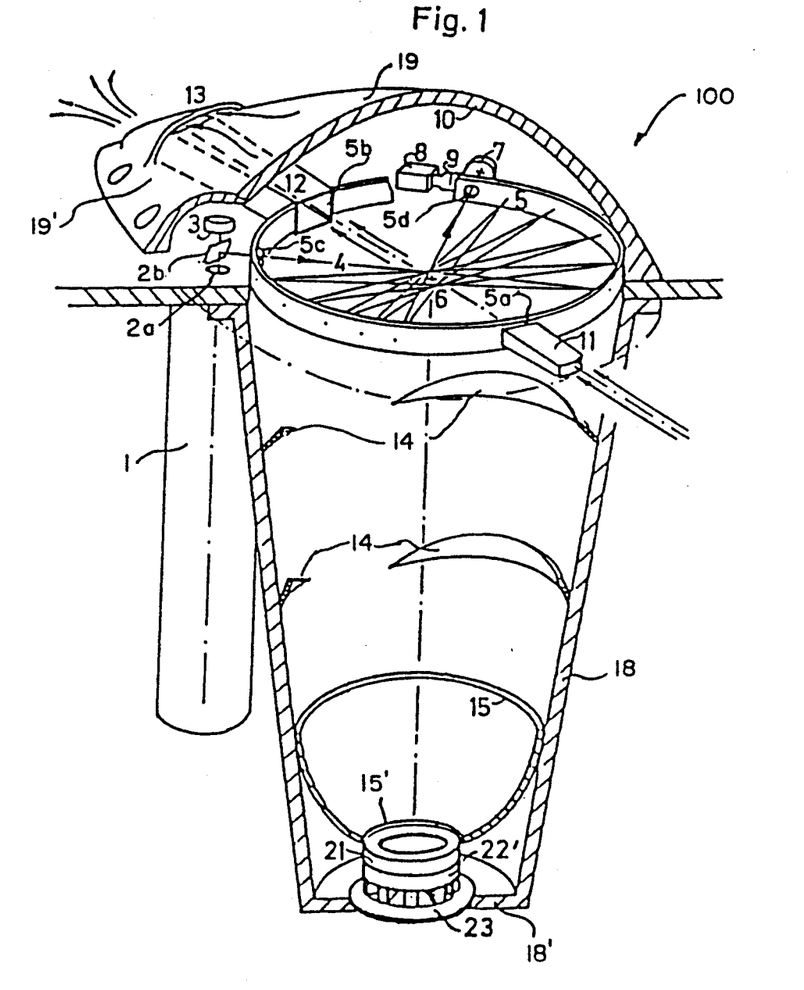
FIG. 1, partly in perspective view and partly in a sectional view, schematically shows a preferred embodiment of a measuring instrument according to the invention.

In FIG. 1, a preferred exemplary embodiment of the extinction meter, identified overall by reference numeral 100, is shown, which in the upper portion of FIG. 1 is seen substantially in perspective, and the lower portion of which is shown substantially as a sectional view. A resonance absorber 23 is preferably secured to the bottom 18' of a frustoconical housing 18 of the extinction meter 100; the resonance absorber 23, for instance, has a layer of rubber, with cylindrical or wedge-shaped voids formed beneath it, and a solid metal plate to close it off. Above the resonance absorber 23, a sound detector 22' is attached, which is connected to a light detector 21 in such a way as to be highly acoustically conductive. The light detector 21 and the sound detector 22' are arranged in terms of their three-dimensional measurements such that a sound pulse generates a resonance in the sound detector 22'.

Above the light detector 21 in the interior of the housing is a hollow sphere 15, which has a recess 15' which is open toward the light detector 21, and the inside surface of the recess is designed such that it is highly absorbent, for instance being anodized such that it has a black, matte, and smooth finish and which has a low coefficient of adhesion to lessen its capacity for being wetted by dirty water. Opposite the recess 15', the hollow sphere 15 merges with the housing 18 embodied as a straight truncated cone, the inside surface of which is likewise made highly absorbent, for instance, again being anodized black, matte and smooth, and once again having a low coefficient of adhesion to reduce wetting with dirty water.

As is schematically suggested in FIG. 1, crescent-shaped, approximately semicircular baffles 14 that taper toward the inside project from the inner wall of the housing 18, with their maximum projection at right angles to a central axis indicated by dot-dash lines; the function of these baffles will be described in further detail hereinafter.

A preferably circular-cylindrical annular mirror 5 of low height is disposed at the upper end of the frustoconical housing 18 as seen in FIG. 1, and above it part of a rotationally symmetrical ellipsoidal mirror 10 is disposed, shown cut away and in perspective. The ellipsoidal mirror 10 mounted above the annular mirror 5 is dimensioned such that its first focal point 6, the upper one as seen in FIG. 1, is located at the center of the central plane of the circular-symmetrical annular mirror 5, while its second focal point is located in the middle of and on the light detector 21 and above the sound detector 22'.

An inlet slit 5a and an outlet slit 5b are provided diametrically opposite one another in the circular-cylindrical annular mirror 5. An inlet nozzle 11 protruding outward from the annular mirror 5 is provided at the inlet slit 5a; the inlet nozzle 11 is black on the inside and widens conically toward the annular mirror 5. An outlet nozzle 12, likewise protruding outward from the annular mirror 5, is mounted on the diametrically opposed outlet slit 5b, and again is black on the inside but on the outside widens conically toward the outside or, in other words, in the direction away from the annular mirror 5. In a continuation of the outlet nozzle 12, an upper housing part 19, that follows the form of the ellipsoidal mirror 10 and hence is streamlined, merges with a part 19' that flattens out toward the end, above which there is a hood 13, of hoop-like shape in plan view; the hood 13 is open at the back, as indicated in FIG. 1 by a plurality of arrows diverging from one another.

A perforated plate or inlet slit 5c and an outlet slit 5d are also embodied in the annular mirror 5. Downstream of the outlet slit 5d, in terms of the radial direction of the annular mirror 5, is an optical detector 7, with a perforated plate not shown in further detail, the diameter of which is smaller than that of the outlet slit 5d. Between the outlet slit 5d in the annular mirror 5 and the detector 7, a calibration standard 9 is provided, which has an optical and acoustical scattering body, to be described hereinafter in further detail, as a reflector, and can be positioned precisely downstream of the outlet slit 5d by means of a solenoid 8.

Radially downstream of the perforated plate 5c outside the annular mirror 5, a beam splitter 2b is provided, which has low transmission but high reflection. In FIG. 1, an optical detector 3 is provided above the beam splitter 2b, and a perforated plate 2a is provided below the beam splitter 2b. Under the perforated plate 2a, FIG. 1 schematically shows a pulse or modulated laser 1, a tunable laser or a tunable laser diode, which serves as a light source of a light emitter; known devices for varying or doubling the frequency, or devices which have discontinuously adjustable frequency intervals of discrete frequencies, are associated with the laser or laser diode 1.

Radiation of sufficiently low divergence emitted by the pulsed or modulated laser 1, for example, travels via the beam splitter 2b and the inlet slit 5c to enter the circular cylindrical annular mirror 5, in which it is multiply reflected; the various ray segments 4 break concentrically about the upper focal point 6 of the ellipsoidal mirror 10. Via this focal point 6, an aerosol to be measured, or attenuating gas or the like, is carried in the direction from the inlet nozzle 11 to the outlet nozzle 12.

Upon measurement, scattered light originating in the vicinity of the upper focal light 6, or in other words originating from a test volume, that is located at the focal point (or + as shown in the drawing) of the folded ray segments 4, is reflected toward the second focal point of the ellipsoidal mirror 10, or the sound pulse and optionally infrared radiation generated upon absorption are reflected to the second focal point of the ellipsoid as well via the ellipsoidal mirror 10, or in other words over virtually the entire hemisphere. The energy contained in the scattered light is then measured directly by the light detector 21.

The measure the absorbed and thus converted radiation component, various embodiments will be disclosed hereinafter, depending on the particular intended use. This can include measurement of the absorption as a thermoacoustical process, which is based on an optical excitation and absorption, and which is then followed by an optical or acoustical detection. At the beam splitter 2b, which has a low transmission but a high reflection splitter, the radiation emitted by the laser 1 is split in such a way that a portion is measured by the detector 3 disposed downstream of the beam splitter, while the other portion, as described above, enters through the inlet slit 5c into the annular mirror 5. After n reflections at the annular mirror, the beam passes at its end of its course through the outlet slit 5d in the annular mirror 5 to leave this mirror and thereby reaches the detector 7 disposed at a suitable angle with respect to the beam axis; as a result, the unavoidable reflection radiation at the detector 7 exits.

In other words, in the embodiment shown in FIG. 1 of the extinction meter according to the invention, no directional radiation is reflected directly via the ellipsoidal mirror 10. Moreover, this system then is designed to be intrinsically extremely low in vibration and it is supported in a damped manner in its entirety.

In the event of a calibration, which can be performed automatically with the aid of a timing unit and/or can be performed manually, the last ray segment 4 of the arriving pulse or modulated radiation, after passing through the outlet opening 5d, strikes the calibration standard 9, which is thrust in front of the detector 7 by the solenoid 8. By means of the final ray segment 4, a defined simulated, lobe-shaped scattered light is generated at the calibration standard 9, and as a result of an absorption, a sound pulse or a thermal signal is reflected via the ellipsoidal mirror 10 to the light detector 21 or to the sound detector 22' or to an infrared detector as well; the reflection here is distributed approximately in accordance with Lambert's law. Moreover, the dimension and shape of the calibration standard 9 can be selected such that for the acoustical excitation, resonance prevails.

In the so-called transmitted light method, the calibration standard 9 may also be disposed as a transparent scattering or absorber disk in front of the outlet slit 5c. If the so-called incident light method is used, the calibration standard 9 may be disposed at an inclination of 45° with respect to the first ray segment 4 in the form of a reflector in front of the outlet slit 5c, so that it points directly toward the detectors 21 and 22.

For instance, using the transmitted light method, the calibration standard can take the form of a hollow sphere, with one opening each for the incident light pulse and for the outgoing light and acoustical pulse. If the incident light method is used, then for an ultrasound resonance, for example, a honeycomb arrangement of small hollow hemispheres can be used.

Figure 2:
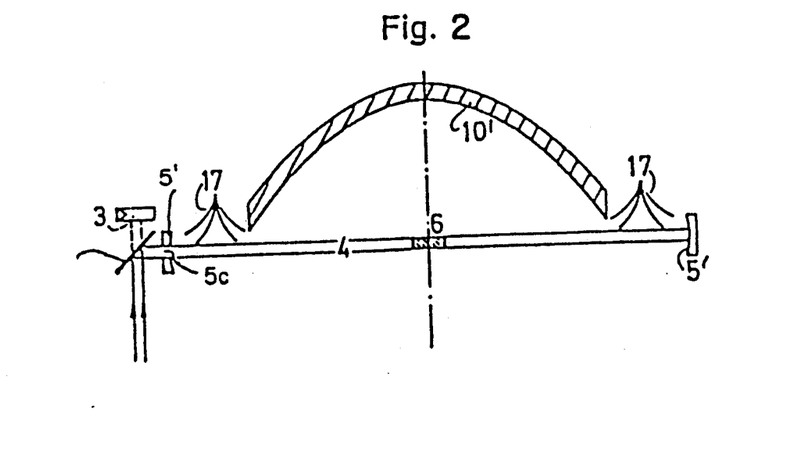
FIG. 2 is a sectional view of an advantageous further feature of the upper part of the embodiment of FIG. 1.

FIG. 2 is a sectional view of an advantageous further feature of the upper part of the embodiment shown in FIG. 1 of the extinction meter according to the invention. Unlike the embodiment of FIG. 1, an annular mirror 5' has a curved inside surface, the curvature of which, symmetrically to the annular mirror center face, is approximately on the order of magnitude of the annular mirror diameter. Also, as FIG. 2 shows, the upper portion of an ellipsoidal mirror 10', in the vicinity of an imaginary line of contact of the ellipsoidal mirror 10' with the annular mirror 5', has a smaller diameter than the annular mirror 5'. As a result, so-called double light traps 17 are formed at edges of the ellipsoidal mirror 10' facing the imaginary annular mirror center face. By the provision of these double light traps 17, interferring radiation arriving diffusely from the annular mirror 5' is prevented from being reflected via the ellipsoidal mirror 10', for instance, to the light detector 21.

The annular mirror 5', which "folds" the parallel radiation originating in the laser 1 reflects this radiation to a certain extent, because of unavoidable errors and an equally unavoidable smudging, to the double light trap 17, which is preferably horn-shaped and thereby absorbs the interfering radiation to an increasing extent toward the tip. This is why, as already noted, no interfering radiation reaches the ellipsoidal mirror 10'. Any interfering radiation in another direction is absorbed via the baffles attached to the interior of the housing 18, via the housing interior itself, and via the hemisphere 15 disposed at the lower end of the housing 18.

The aforementioned double light traps 17 are each disposed upstream and downstream of each ray segment 4 in such a way that the ray segments 4 just miss touching the edge. After a great enough number of n reflections at the annular mirror 5', the ray segment in the annular mirror 5' finally exits from the annular mirror through the perforated plate or outlet slit 5d and is measured by means of the detector 7. Since the optical axis of the detector 7 with respect to the final ray segment 4 is disposed at a small angle, the light reflected by the detector 7 is absorbed in a single light trap, not shown in detail.

From the measured signals of the detector 21 and from the geometric mean of the signals of the detectors 3 and 7, the quotient is formed with the aid of a multifunction converter, for instance; when weighted, this quotient represents the spectral scattering coefficient, and this value, along with an indication of the emitter wavelength used, is displayed directly on the equipment. These values are then available for remote display or for reproduction by means of a plotter, and the original values are also available for further computer processing and subsequent storage, for instance on tape.

Moreover, by means of the output signal of the detector, the operating state of the measuring instrument according to the invention is shown, by the display on the part of the detector of a value based on the spectral sensitivity of the detector, this value being equivalent to the adjusted wavelength of the light emitter. This actual value, which is compared with the set-point value or with a constant quotient of the measured values of the detectors 3 and 7, permits an assessment of malfunction-free operation to be made.

On the other hand, in a calibration process, as soon as the solenoid 8 is subjected to electric current, a zero or null signal, or the noise value of the detector 7, is displayed directly via a display means and is simultaneously available for remote display and further processing (calibration!).

Furthermore, in the measuring instrument 100 according to the invention, the acoustic intensity of a sound pulse that is produced in the aerosol upon the absorption of the beams of light from the emitter is reflected from the focal point 6, within the solid angle of the ellipsoid mirror 10 which presents virtually the hemisphere, is reflected to its second focal point; the energy arriving at the second focal point is carried directly onward via acoustical detectors 22' or is measured indirectly by means of optical methods. In this process, the acoustical radiation can be separated from the optical radiation beforehand by means of some device. The absorption coefficient can be formed and recorded analogously to the method described above.

Further, according to the invention, the propagation of the pulse, for instance in the receiving detector 22', by comparison with the emitted pulse can be displayed as a quotient in the detector 3 or 7; more precisely, its temporal resolution is recorded. For the sake of an assessment or a display relating to the increasing or decreasing averaged radii of the absorbing aerosol, the increasing or decreasing propagation can also be recorded or displayed. In this process, the particle size distribution with respect to the absorption is ascertained via the variation in the throughput of the measured gas, or with the aid of a variation in the pulse duration.

A correction factor, which is necessary for determining the scattering coefficient, is dependent in this context not only on the deficit angle, that is, the missing angle toward 0° as well as toward 180° that includes the hemisphere, but also on the absolute volumetric scattering function, or on a particle size distribution of the particular aerosol or gas present. The relative deviation of the correction factor of conventional nephelometers is on the order of magnitude of ±10% of the mean value. To keep this systematic error small, the aforementioned deficit angle is kept small in the apparatus of the invention by structural provisions. By using various correction factors for intervals of the measured value range, or by correction as a function of the measured value, the relative deviation of the correction factor can be reduced with the aid of additional computations.

In the measuring instrument according to the invention, as a result of the determination of the scattering or absorption coefficient via the quotient of the signal of the detector 21 or 22' and via the geometric mean of the signals of the detectors 3 and 7, a second correction factor is obtained, which is dependent on the geometry of the optics as well as on the number of reflections n at the annular mirror 5 or 5', and can advantageously be designed without computations, such that the systematic error in the quotient of these two correction factors, namely those obtained from the deficit angle and from the reflection factor, assumes a minimum of the systematic error over a wide range of the measured value range and provides high accuracy in the measured values.

When the measuring instrument according to the invention is used, both the scattering and absorption coefficient, as a function of the signals of the linear detectors 3, 7 and 21 or 22', and an instrument-specific constant are obtained. For checking and supplementation in the case of large extinction coefficients, the range that can be considered a transmissometer is additionally used, which permits measurement of the transmission via the folded ray path of the annular mirror 5 with the aid of the detectors 3 and 7. In that case, however, the radiant reflectance of the annular mirror 5 must be determined beforehand.

Figure 3:
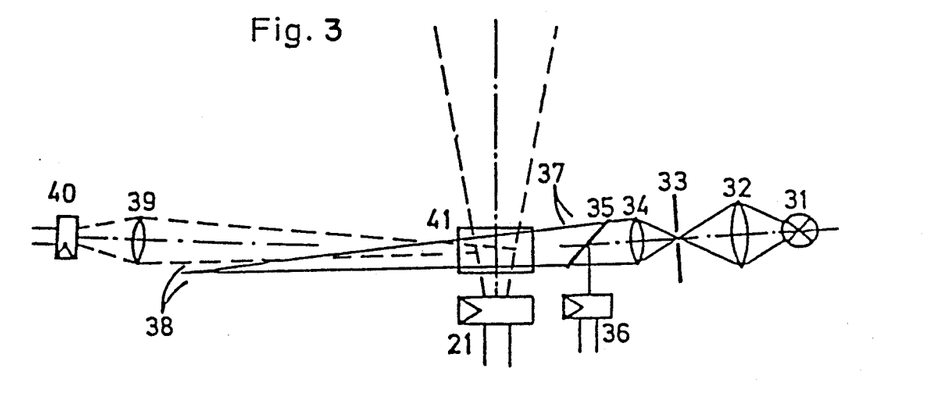
FIGS. 3 and 4 show preferred embodiments of control converters for the measuring instrument according to the invention as shown in FIGS. 1 and 2.
Figure 4:
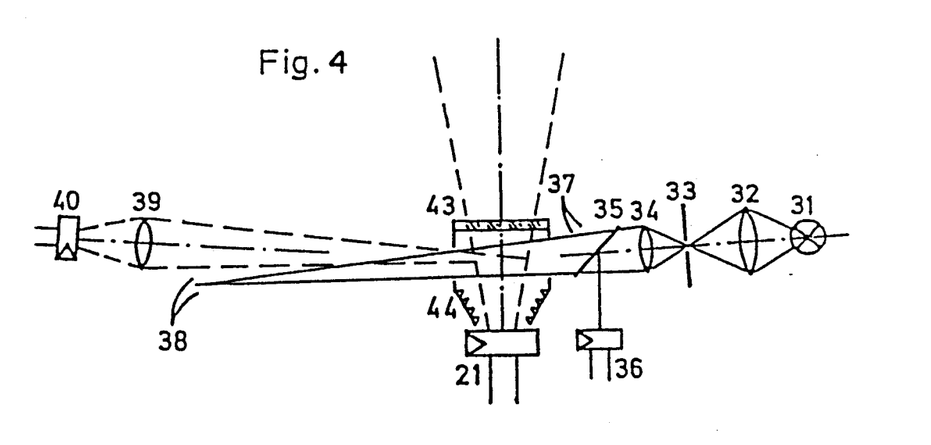

In FIGS. 3 and 4, preferred control transducers are shown, with which a much larger output signal than the input signal can be generated, and in which a feedback of the output signal to the input signal or to the measured signal is possible, when the output signal is transformed into the measured signal.

In FIG. 3, in the other focal point of the ellipsoidal mirror 10, instead of the detector 22' of FIG. 1 a transparent acoustical resonance body 41 is provided, which is preferably filled with a liquid or a dispersion; this resonance body 41, for instance a Debye-Sears type, is set to resonating upon the arrival of a sound pulse.

Approximately vertically to the center axis of a cone formed by the sound pulse, a monochromatic light source 31 such as a light emitting diode, a condenser lens 32 which projects the light source to a gap 33, and a lens 34 are provided in succession, that is, in that order in the direction of propagation of the light. Via an ensuing beam splitter 35 and the transparent acoustical resonance body 41, in the exemplary embodiment of FIG. 3, or via a resonance housing 44 for instance in the form of a schlieren housing, in the case of the exemplary embodiment of FIG. 4, the lens 34 projects the gap 33 onto a light trap 38 provided on the other side of the resonance body 41 or resonance housing 44; the light trap 38 is disposed in the primary axis of the lens 34.

In FIGS. 3 and 4, an optical detector 36 is in each case disposed under the beam splitter 35, and continuously measures the radiant intensity of the light source 31 and hence its constancy. A further light trap 37 is also provided above the beam splitter, and is adjusted such that no direct light reaches a further light detector 40, in front of which a collecting lens 39 is disposed in such a way that the aforementioned primary axis of the lens 34 and the primary axis of the collecting lens 39 form a very small angle with one another.

By means of the collecting lens 39, the light from the center of the acoustical resonance body 41 in the case of the embodiment of FIG. 3 and the resonance housing 44 in the embodiment of FIG. 4 are projected onto the light detector 40. In both embodiments, the spacing between the resonance body 41 of FIG. 3 or the resonance housing 44 of FIG. 4 and the lens 39 is substantially greater than the spacing between either resonance means and the lens 34.

In the embodiment of FIG. 4, the resonance housing 44 is provided with lateral windows in the normal direction to the lens 34 and on the other side in the direction toward the collecting lens 39, so that gases or liquids can be accommodated in the resonance housing; on the side remote from the light detector 21, a thin, transparent cover plate 43 is provided on the resonance housing 44. The spacing of the cover plate 43 with respect to this light detector 21 can be adjusted and set accurately, for instance via a fine screw thread, not shown in further detail.

If scattered radiation is now reflected via the ellipsoidal mirror 10 out of the vicinity of the focal point 6 (this vicinity can also be called the test volume), then this scattered radiation passes through the transparent resonance body 41 or via the transparent cover plate 43 and the resonance housing 44 to reach the light detector 21. An acoustical pulse, which is produced in the test volume in the vicinity of the focal point in the absorption of a radiation emitted for instance by a laser 1, then likewise reaches the acoustical resonance body 41 (see FIG. 3), where it effects a periodical variation in thickness and a variation in the index of refraction, similarly to what happens in an optical refraction grating. As a result, the light emitted by the light source is then correspondingly refracted and measured by the light detector 40, than the exemplary embodiment of FIG. 4, because of the change in thickness combined with a very flat incidence of the light from the light source 31, a deflection of this light beam takes place in the resonance housing 44, which for instance may be embodied as a schlieren housing and which, particularly if a telephoto lens of long focal length is used as the collecting lens 39, furnishes correspondingly good signals at the light detector 40, as a standard for the absorption.

Moreover, a modified interferometer of the Fabry/Perot type may be provided; in that case, an upper glass plate is set to resonating by the acoustical pulse, while a lower glass plate remains immobile. The vibration of the upper glass plate brings about a variation in the response difference and hence a variation in the interference bands.

Figure 5:
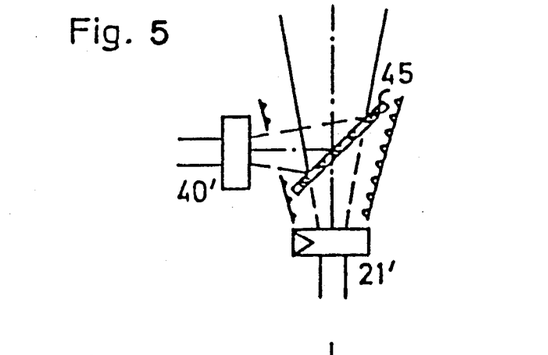
FIGS. 5–8 show preferred embodiments of genuine converters for the embodiments of the measuring instrument according to the invention shown in FIGS. 1 and 2.

In FIGS. 5–8, further so-called genuine converters are shown in accordance with the embodiment of FIG. 1. In the embodiment of FIG. 5, above the one detector 21' retained indirectly on the housing bottom 18', an optical-acoustical beam splitter plate 45 is oriented at an angle of 45° with respect to the center axis of the radiation; the optical and acoustical radiation striking the detector 21' vertically is split and distributed by this beam splitter plate 45 to both the detector 21' and the detector 40'. With the exemplary embodiment of FIG. 5, accordingly, two different measurement procedures can be performed.

In the one case, the arriving scattered radiation is separated by the optical-acoustical beam splitter plate 45 from an arriving sound wave or infrared radiation generated by absorption; then, either the light radiation is reflected and determined with the detector 40', which in that case functions as a light detector, and the transmitted scattered radiation, in the form of a sound wave or infrared radiation, is measured with the detector 21 which in that case functions as a sound or infrared detector, or vice-versa. In the first case, the sound wave resistance of the beam splitter plate 45 should be kept low, which can for instance be done with a mirrored, thin, lightweight plastic plate, by utilizing the coincidence effect.

In the other case, by means of the opto-acoustical beam splitter plate 45, analogously to the above case, the scattered radiation is separated from the acoustic pulse generated in the absorption. Here, the beam splitter plate 45 should be selected with a sufficient acoustical thickness, in accordance with the sound wavelength, with a view to the penetration depth of sound waves, in order to avoid partial reflection. As the beam splitter plate 45, a plate made from a heavy type of glass with a reflection-reducing coating can then be used.

Figure 6:
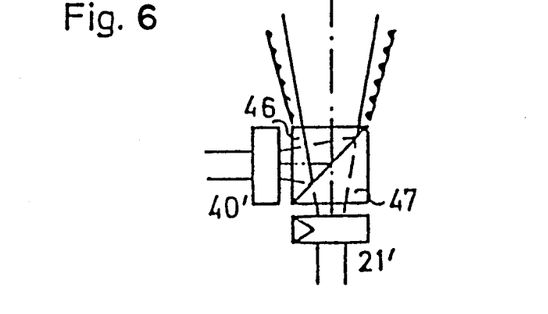

In the embodiment of FIG. 6, the acoustical radiation is separated from the optical radiation not with the beam splitter plate 45 but instead with the aid of an optical-acoustical beam splitter cube, which is made up of an upper beam splitter prism 46 and a lower beam splitter prism 47. The optical-acoustical radiation here arrives approximately vertically at the upper prism 46 and emerges from the lower prism 47. Analogously to the embodiment of FIG. 5, once again two options are available, depending on the suitable selection of material for the upper prism 46 and lower prism 47; in each case, in terms of the surface, an approximately vertical entry and exit of the light is assumed.

For a completely optical radiation, the indexes of refraction of the two prisms 46 and 47 are the same, while the wave resistance of the two prisms 46 and 47 for the acoustical radiation are so different that total reflection occurs for the acoustical wave at the lower prism 47, which has an acoustically thinner medium. If the types of radiation are reversed, then the wave resistance of the two prisms 46 and 47 for the acoustical radiation should be selected to be equal, and the indexes of refraction are so different that total reflection for the optical radiation occurs in the lower prism.

Figure 7:
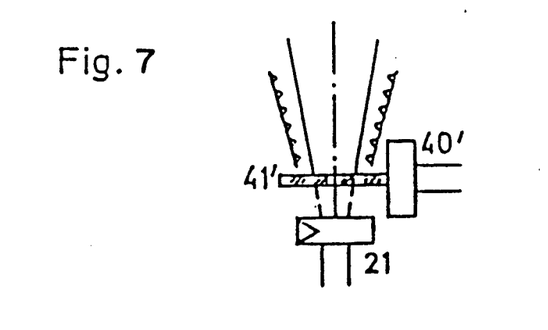

In the embodiment of FIG. 7, a transparent acoustical resonance plate 41' is disposed a short distance upstream of the optical detector 21, and carries an optical reflection-reducing coating; with its narrow end, the resonance plate is connected in a sound-conducting manner with the acoustic detector 40'. The transparent acoustic resonance plate 41' may also be embodied in two halves, in which case the trapped air, as a resonator, communicates with the acoustical sound detector 40'. With the aid of the transparent acoustical resonance plate 41' that vibrates with acoustical resonance, the acoustical radiation is then measured directly at the acoustical sound detector 40' that is thus firmly connected to the resonance plate. The optical radiation is transmitted by the resonance plate 41' and then measured at the light detector 21.

Figure 8:
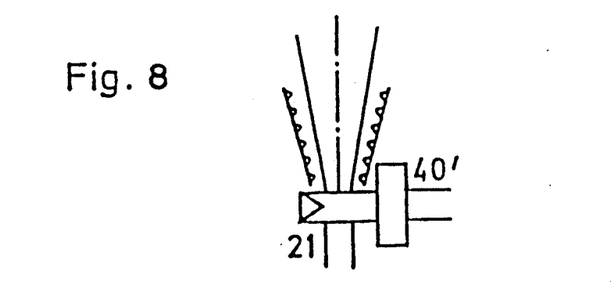

In the embodiment of FIG. 8, the sound detector 40' is connected in an acoustically conductive manner directly with the light detector 21. Here, the light radiation is measured directly by the light detector 21, while the acoustic detector 40' connected laterally to the detector 21 measures the acoustic radiation via this light detector 21, similarly to the case with the embodiment of FIG. 1, in the form of structure-borne sound.

A further provision will now be described for minimizing disturbance of the test gas, for example using the embodiment of FIG. 1. As can be seen from FIG. 1, test gas or air to be measured flows through the extinction meter 100 via the conical inlet nozzle 11, the inlet slit 5a, the focal point 6, the outlet slit 5b and the conical outlet nozzle 12; the two nozzles 11 and 12 each widen in the flow direction. The test gas or air is forced into the inlet nozzle 11 either by the motion of the extinction meter, which for instance is mounted on a vehicle, in the form of a motor vehicle or an aircraft, or in the case of a test gas in repose is forced into the inlet nozzle 11 by being fanned.

The gas flowing via the streamlined external shape of the ellipsoidal mirror 10 then aspirates the gas to be tested out of the outlet nozzle 12 with a suction that is equal to the pressure loss from the inlet nozzle to the outlet nozzle; this aspiration takes place through the narrowing, hoop-like hood 13, which is embodied in the form of a wing-tip slot and functions accordingly. In other words, if the hoop-like hood 13 is dimensioned correctly, the suction compensates for the delay and the pressure rise resulting from the enlargement in the cross section of the inlet and outlet nozzles 11 and 12 and from the friction losses in the interior of the extinction meter 100. As a result, the gas pressure in the test volume differs only minimally from the unimpeded pressure of the test gas; hence the aerosol of the test gas in the test volume, that is, in the vicinity of the focal point 6, is interfered with only negligibly and thus is affected only minimally.

Contamination or soiling of the extinction meter 100 with test gas should be avoided, not only because of the additional maintenance that entails, but also to assure that precisely defined conditions will always prevail in the extinction meter; such contamination can be avoided virtually entirely in the extinction meter 100 according to the invention by means of the structural features provided in it.

A stream of gas moving from the inlet nozzle 11 to the outlet nozzle 12 forms a ring of turbulence about itself in the interior of the volume of the extinction meter 100. The gas forming this vortex does not mix with the gas stream flowing straight through, which traverses the focal point region 6 and thus embodies the volume to be measured. The energy that is consumed by friction at the wall is returned to the vortex from the gas flow that generates it, because of the action of the hoop-like hood 13 disposed at the end 19', which tapers off to a flat shape, of the upper housing part 19.

The vortex that moves from the inlet nozzle 11 to the outlet nozzle 12 does not reach the wall, since the motion is increasingly slow, and the ring of turbulence tends to enlarge continuously, while the cross section tends to decrease and the angular velocity tends to increase. The vortex is guided by the baffles 14 disposed at a right angle to the longitudinal axis, shown in dot-dash lines, of the extinction meter 100; these baffles 14 taper in crescent fashion on the conical inner wall of the housing 18 of the extinction meter 100 with a slight inclination with respect to the focal point 6 and rise slightly, toward the outlet nozzle. The ring of turbulence that moves toward the outlet nozzle 12 is thus guided through the baffles 14 in such a way that its diameter decreases. Thus the ring of turbulence cannot approach the wall, and can neither increase its diameter nor decrease its cross section. This stabilizes the turbulence and makes it longer-lasting; moreover, mixing of the through-flowing test gas with the turbulence is minimized. A second advantageous property of the stabilized turbulence is that a sound wave moving through the core of the turbulence undergoes a deflection first in one direction and then an equal deflection in the other direction, as seen from above, and thus in a sense pases through the ring of turbulence without disturbance.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A measuring instrument for determining the scattering and absorption coefficient of the atmosphere, comprising:
    an emitter side comprising a light emitter having a light source which is a pulsed laser, and a device for varying the frequency associated with the laser;
    an annular mirror (5) having an inlet slit (5a) and a first diametrically opposed outlet slit (5b) for the introduction and exiting of aerosol gas to be measured;
    a receiver side having alight detector (27) and a sound detector (22') for receiving emitter light attenuated in the atmosphere;
    a rotationally symmetrical ellipsoidal mirror (10) disposed such that a first focal point (6) of the ellipsoidal mirror is located in a substantially center point of a substantially center plane of the annular mirror (5) and a second focal point is located in a substantially middle position of the light detector (21) and the sound detector (22') associated with the light detector (21), and
    wherein the light detector and the sound detector (22') are accommodated in a fluidicly shaped space, so that radiation of small divergence emitted by the light emitter is reflected a multiplicity of times, after introduction thereof into the annular mirror (5), ray segments of light reflected by the annular mirror interest concentrically about the first focal point (6) of the ellipsoidal mirror (10), and the attenuating gas to be measured are carried, via the first focal point (6) from the inlet (5a) slit to the first outlet slit (5b).

2. An instrument as defined by claim 1, further comprising:
    a frustoconical housing 18 surrounding the fluidicly shaped space;
    a resonance absorber (23) securing the sound detector (22') to a bottom surface (18') of the frustoconical housing (18), and
    wherein the light detector (21) is secured in a sound-conducting manner on the sound detector (22').

3. An instrument as defined by claim 1, further comprising:
    a first perforated plate (2a) and a beam splitter (2b) for dividing radiation emitted by the laser or laser diode, said beam splitter (26) being of a low transmission and high reflection;
    a first optical detector (3) disposed downstream in the radiation direction with respect to the beam splitter (2b) for detecting one part of the laser radiation;
    a second perforated plate (5c) disposed in the annular mirror (5) through which (5c) another part of the radiation passes;
    a second optical detector, disposed down-stream in the radial direction of the annular mirror (5) to a second outlet slit (5d) in the annular mirror;
    wherein the another part of the radiation is formed into a beam and directed downstream after n reflections in the annular mirror (5); and after exiting through the second outlet slit (5d) in the annular mirror (5) toward the second optical detector (7), which detector (7) forms an angle with an axis of the beam.

4. An instrument as defined by claim 1, wherein an inside surface of the circular annular mirror (5'), symmetrically to its center face, has a curvature on the order of magnitude of the annular mirror diameter, the annular mirror diameter is greater than the diameter of the ellipsoidal mirror (10'), and an edge of the ellipsoidal mirror above the surface of the annular mirror 5 is embodied as a double light trap (17), so as to suppress interfering radiation arriving diffusely from the annular mirror (5') and reflected via the ellipsoidal mirror (10') to the light detector (21).

5. An instrument as defined by claim 1, further comprising a calibration (9) standard disposed between a second outlet slit (5d) in the annular mirror (5) and the second optical detector (7) and having an optical and acoustical scattering body as a reflector, the calibration standard being positionable by means of a solenoid behind the outlet slit precisely in such a way that the arriving pulsed radiation is defined and reflected with a distribution approximately in accordance with Lambert's law, and the proportion of the absorbed radiation that is partly converted into acoustical radiation is correspondingly projected in a defined manner via the second outlet slit (5d), with a distribution of energy approximately in accordance with Lambert's law, onto the opposite rim of the ellipsoidal mirror (10) and from there is reflected to the second focal point thereof.

6. An instrument as defined by claim 1, wherein the upper part of the measuring instrument (100) is embodied in streamlined fashion, further comprising an inlet nozzle (11) that is black on the inside and widens conically toward the annular mirror (5) for introducing the provided on an outside of the inlet slit (5a) in the annular mirror (5), and an outlet nozzle (12), which is likewise black on the inside and widens conically toward the outside, provided on the outside of the first outlet slit (5b) diametrically opposite the inlet slit (5a), an upper housing (19) having a part which tapers to a flat shape covering the outlet nozzle (12), a hoop-like hood (13) functioning like wing-tip slot embodied near an end of the upper housing part (19') tapering to a flat shape for the aspiration of the gas flowing through the outlet nozzle (12).

7. An instrument as defined by claim 1, further comprising:
- a hollow sphere (15) for closing off the fluidic shaped space in the interior of the frustoconical housing via the bottom surface (18') thereof, said hollow sphere (15) being highly absorbent on the inside and having a low coefficient of adhesion, the sphere 15 having a recess for receiving the detectors (21, 22') attached to the housing bottom (18') and opposite the recess (15') merging with an absorbing, straight truncated cone having a low coefficient of adhesion;
- crescent-shaped, approximately semicircular baffles (14) protruding from the cone tapering inward at ends thereof, and
- wherein the baffles (14) having their greatest projection at right angles to a connecting line between the inlet and outlet nozzles (12) and are oriented inclined toward the first focal point (6), and in the direction of the outlet nozzle (12) the baffles rise by a few angular degrees with respect to the straight connecting line between the inlet (11) and outlet nozzles (12).

8. An instrument as defined by claim 1, wherein the inside of the ellipsoidal mirror, the annular mirror and the beam splitter are heatable in such a manner that their temperature always remains somewhat above the temperature of the ambient air, and the detectors and the light source are designed in temperature-stabilized fashion.

9. An instrument as defined by claim 1, further comprising:
- a transparent, acoustical resonance means (41) disposed upstream of the light detector (21) in the path of a sound pulse reflected from one focal point to the other of the ellipsoidal mirror (10), the resonance body being filled with a liquid or a dispersion;
- a monochromatic light source (31), a condenser lens (32), a diaphragm (33) forming an optical gap and a lens (34) disposed in that order in the light propagation direction approximately at right angles to the center axis of a sound formed by the acoustical pulse, on one side of the resonance body (41);
- a light trap (38) and a collecting lens (39) with a following light detector (40) disposed on the opposite, other side of the resonance body in the primary axis of the lens (34), and
- wherein the primary axis of the lens and the primary axis of the collecting lens form a very small angle, and the spacing between the resonance body (41) and the light trap (38) is substantially greater than the spacing between the resonance body (41) and the lens (34).

10. An instrument as defined by claim 9, further comprising a third optical detector (36) disposed below a second beam splitter (35) provided between the lens (34) and the resonance body (41) for measuring the constancy of the light source (31), and a second light trap (37) associated with the second beam splitter (35) and the third optical detector (36) for radiation limitation.

11. An instrument as defined by claim 9, wherein the transparent, acoustical resonance body comprises a resonance housing (44) for gases or liquids provided with side windows both in the direction toward the lens (34) and in the direction toward the collecting lens (39), and a transparent cover plate (43) on the side remote from the light detector (27), the spacing of which with respect to the light detector (21) being finely adjustable.

12. An instrument as defined by claim 1, further comprising an optical-acoustical beam splitter plate (45) oriented at substantially 45° from the center axis of the radiation is provided above the detector (21') retained on the housing bottom (18'), the optical and acoustical radiation vertically incident upon the detector (21) being distributed by the beam splitter plate (45) to the detector and a second detector.

13. An instrument as defined by claim 12, wherein the beam splitter plate (45) is a lightweight, thin, mirrored plastic plate having a low sound wave resistance, and the detector (21) is a sound detector and the second detector (40') is a light detector.

14. An instrument as defined by claim 12, wherein the beam splitter plate is a heavy glass plate (42) with a reflection-reducing coating, and the detector is a light detector and the second detector is a sound detector.

15. An instrument as defined by claim 12, wherein the beam splitter plate (45) comprises an opto-acoustical beam splitter cube comprising an upper prism (46) and a lower prism (47).

16. An instrument as defined by claim 15, wherein as soon as the sound wave resistance of the two prisms (46), (47) is approximately identical, the difference in the optical indexes of refraction is selected such that total reflection occurs at the lower prism (47).

17. An instrument as defined by claim 15, wherein as soon as the optical indexes of refraction are identical, the difference in the acoustical indexes of refraction is selected such that for the acoustical wave at the lower prism (47) having an acoustically lightweight medium, total reflection occurs.

18. An instrument as defined by claim 1, further comprising a transparent acoustical resonance plate (41') is disposed upstream of the optical detector (21) parallel to and spaced slightly apart therefrom, the resonance plate (41) having an optical reflection-reducing coating and being connected at one narrow end in a sound-conducting manner to the sound detector (40').

19. An instrument as defined by claim 18, wherein the transparent acoustical resonance plate (41') is embodied in two halves, and the trapped air, as a resonator, is connected to the sound detector.

20. An instrument as defined by claim 1, wherein the sound detector (40') is attached in a sound-conducting manner to the side of the light detector (21), and is secured at the back, via a resonance absorber, to the frustoconical housing.

* * * * *